US011633534B2

(12) United States Patent
Bakken

(10) Patent No.: US 11,633,534 B2
(45) Date of Patent: Apr. 25, 2023

(54) ANGIOGRAM INJECTIONS USING ELECTROCARDIOGRAPHIC SYNCHRONIZATION

(71) Applicant: ACIST Medical Systems, Inc., Eden Prairie, MN (US)

(72) Inventor: Matthew James Russell Bakken, Bloomington, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 219 days.

(21) Appl. No.: 16/996,083

(22) Filed: Aug. 18, 2020

(65) Prior Publication Data

US 2022/0054735 A1    Feb. 24, 2022

(51) Int. Cl.
*A61M 5/00* (2006.01)
*A61J 7/04* (2006.01)
*A61M 5/168* (2006.01)

(52) U.S. Cl.
CPC ............ *A61M 5/007* (2013.01); *A61J 7/0481* (2013.01); *A61M 5/1684* (2013.01);
(Continued)

(58) Field of Classification Search
CPC ................ A61M 5/007; A61M 5/1684; A61M 5/16877; A61M 5/16886;
(Continued)

(56) References Cited

U.S. PATENT DOCUMENTS 2,627,270 A    2/1953   Glass
4,044,757 A    8/1977   McWhorter et al.
(Continued)

FOREIGN PATENT DOCUMENTS

CN    87202114 U    4/1988
CN    1617686 A     5/2005
(Continued)

OTHER PUBLICATIONS

Partial International Search Report dated Nov. 17, 2021 for related International Application No. PCT/US2021/046086, 12 pages.
(Continued)

*Primary Examiner* — Nilay J Shah
(74) *Attorney, Agent, or Firm* — Crowell & Moring LLP

(57) ABSTRACT

An injection system is described that receives, from one or more sensors, a first group of one or more signals indicating a current volume of injection fluid dispensed from a fluid reservoir at a first time. The injection system determines, based on the first group of one or more signals, that a difference between a dispensed volume limit and the current volume of the injection fluid dispensed from the fluid reservoir at the first time is less than a necessary volume of fluid required to complete both a systolic injection phase and a diastolic injection phase. The injection system further, responsive to determining that the difference is less than the necessary volume of fluid required to complete both the systolic injection phase and the diastolic injection phase, controls the injection system to refrain from performing each of the systolic injection phase and the diastolic injection phase.

27 Claims, 8 Drawing Sheets

(52) U.S. Cl.
CPC .... *A61M 5/16877* (2013.01); *A61M 5/16886* (2013.01); *A61M 2205/3379* (2013.01); *A61M 2205/50* (2013.01); *A61M 2205/583* (2013.01); *A61M 2230/04* (2013.01)

(58) Field of Classification Search
CPC ...... A61M 2205/3379; A61M 2230/04; A61M 2205/50
See application file for complete search history.

(56) References Cited

U.S. PATENT DOCUMENTS

| | | |
|---|---|---|
| 4,084,606 A | 4/1978 | Mittleman |
| 4,250,887 A | 2/1981 | Dardik |
| 4,462,409 A | 7/1984 | Pace et al. |
| 4,819,684 A | 4/1989 | Zaugg et al. |
| 5,097,841 A | 3/1992 | Moriuchi et al. |
| 5,098,405 A | 3/1992 | Peterson et al. |
| 5,176,658 A | 1/1993 | Ranford |
| 5,190,067 A | 3/1993 | Paradis et al. |
| 5,267,964 A | 12/1993 | Karg |
| 5,573,515 A | 11/1996 | Wilson et al. |
| 5,800,397 A | 9/1998 | Wilson et al. |
| 5,840,026 A | 11/1998 | Uber, III et al. |
| 5,843,044 A | 12/1998 | Moorehead |
| 5,882,343 A | 3/1999 | Wilson et al. |
| 6,050,450 A | 4/2000 | Gardos |
| 6,099,502 A | 8/2000 | Duchon et al. |
| 6,182,698 B1 | 2/2001 | Barak |
| 6,221,045 B1 | 4/2001 | Duchon et al. |
| 6,254,835 B1 | 7/2001 | Feygin |
| 6,344,030 B1 | 2/2002 | Duchon et al. |
| 6,447,481 B1 | 9/2002 | Duchon et al. |
| 6,569,117 B1 | 5/2003 | Ziv et al. |
| 6,638,258 B2 | 10/2003 | Schwartz et al. |
| 6,656,157 B1 | 12/2003 | Duchon et al. |
| 6,708,714 B1 | 3/2004 | Mijers |
| 6,733,477 B2 | 5/2004 | Cowan et al. |
| 6,746,427 B2 | 6/2004 | Duchon et al. |
| 6,752,789 B2 | 6/2004 | Duchon et al. |
| 6,945,959 B2 | 9/2005 | Duchon et al. |
| 7,094,216 B2 | 8/2006 | Trombley, III et al. |
| 7,128,729 B2 | 10/2006 | Duchon et al. |
| 7,153,288 B2 | 12/2006 | Duchon et al. |
| 7,267,666 B1 | 9/2007 | Duchon et al. |
| 7,326,186 B2 | 2/2008 | Trombley, III et al. |
| 7,357,785 B2 | 4/2008 | Duchon et al. |
| 7,389,788 B2 | 6/2008 | Wilson et al. |
| 7,566,326 B2 | 7/2009 | Duchon et al. |
| 7,581,559 B2 | 9/2009 | Bausmith, III |
| 7,610,936 B2 | 11/2009 | Spohn et al. |
| 7,617,837 B2 | 11/2009 | Wilson et al. |
| 7,662,124 B2 | 2/2010 | Duchon et al. |
| 7,703,483 B2 | 4/2010 | Hartman et al. |
| 8,412,312 B2 | 4/2013 | Judell et al. |
| 2002/0065467 A1 | 5/2002 | Schutt |
| 2002/0103437 A1 | 8/2002 | Jibiki |
| 2003/0018252 A1* | 1/2003 | Duchon ................. A61B 6/504 600/432 |
| 2003/0122095 A1 | 7/2003 | Wilson et al. |
| 2005/0230575 A1 | 10/2005 | Zelenski et al. |
| 2005/0234407 A1 | 10/2005 | Spohn et al. |
| 2005/0234428 A1* | 10/2005 | Spohn ................... A61M 5/007 604/533 |
| 2006/0079768 A1 | 4/2006 | Small et al. |
| 2006/0167415 A1 | 7/2006 | Nemoto |
| 2006/0178632 A1 | 8/2006 | Trombley et al. |
| 2006/0180202 A1 | 8/2006 | Wilson et al. |
| 2006/0184122 A1 | 8/2006 | Nemoto |
| 2007/0055202 A1 | 3/2007 | Duchon et al. |
| 2007/0161970 A1 | 7/2007 | Spohn et al. |
| 2007/0167919 A1 | 7/2007 | Nemoto et al. |
| 2007/0179487 A1 | 8/2007 | Tearney et al. |
| 2007/0244435 A1 | 10/2007 | Hicks |
| 2007/0249936 A1 | 10/2007 | Deckman et al. |
| 2008/0086087 A1 | 4/2008 | Spohn et al. |
| 2008/0091142 A1 | 4/2008 | Trombley et al. |
| 2008/0103437 A1 | 5/2008 | Duchon et al. |
| 2008/0161634 A1 | 7/2008 | Nemoto et al. |
| 2008/0183131 A1 | 7/2008 | Duchon et al. |
| 2008/0300483 A1 | 12/2008 | Nemoto et al. |
| 2009/0131765 A1 | 5/2009 | Roschak et al. |
| 2009/0149743 A1 | 6/2009 | Barron et al. |
| 2009/0221914 A1 | 9/2009 | Barrett et al. |
| 2009/0234231 A1 | 9/2009 | Knight et al. |
| 2009/0304593 A1 | 12/2009 | Frinking et al. |
| 2009/0312740 A1 | 12/2009 | Kim et al. |
| 2010/0019178 A1 | 1/2010 | Wilson et al. |
| 2010/0094133 A1 | 4/2010 | Yoshiara et al. |
| 2010/0113924 A1 | 5/2010 | Hajicek et al. |
| 2010/0249588 A1 | 9/2010 | Knight |
| 2011/0071404 A1 | 3/2011 | Schmitt et al. |
| 2011/0071405 A1 | 3/2011 | Judell et al. |
| 2011/0077528 A1 | 3/2011 | Kemp et al. |
| 2011/0196255 A1 | 8/2011 | Kassab |
| 2012/0022360 A1 | 1/2012 | Kemp |
| 2013/0216114 A1 | 8/2013 | Courtney et al. |
| 2014/0121513 A1 | 5/2014 | Tolkowsky et al. |
| 2014/0180083 A1 | 6/2014 | Hoseit |
| 2015/0324962 A1 | 11/2015 | Itu et al. |
| 2017/0325769 A1 | 11/2017 | Venugopal et al. |
| 2021/0244371 A1 | 8/2021 | Zhang |

FOREIGN PATENT DOCUMENTS

| | | |
|---|---|---|
| CN | 101039711 A | 9/2007 |
| CN | 101355975 A | 1/2009 |
| EP | 331526 A1 | 9/1989 |
| JP | 62221335 A | 9/1987 |
| JP | 2001178720 A | 7/2001 |
| JP | 2001245862 A | 9/2001 |
| JP | 2002210007 A | 7/2002 |
| WO | 02064195 A2 | 8/2002 |
| WO | 03050491 A2 | 6/2003 |
| WO | 2005070299 A1 | 8/2005 |
| WO | 2005110007 A2 | 11/2005 |
| WO | 2007062315 A2 | 5/2007 |

OTHER PUBLICATIONS

Bazilevs et al., "From Imaging to Prediction: Emerging Non-Invasive Methods in Pediatric Cardiology," Progress in Pediatric Cardiology, vol. 30, No. 1-2, 2010, pp. 81-89.

Chen et al., "Phase Insensitive Homomorphic Image Processing for Speckle Reduction," Ultrasonic Imaging, vol. 18, Article 0007, 1996, pp. 122-139.

Ledoux et al., "Angle-Independent Motion Measurement by Correlation of Ultrasound Signals Assessed with a Single Circular-Shaped Transducer," Ultrasonic Imaging, vol. 21, 1999, pp. 216-240.

Lupotti et al., "Quantitative IVUS Blood Flow Using an Array Catheter," Computers in Cardiology, vol. 28, 2001, pp. 5-8.

Revell et al., "Computer Vision Elastography: Speckle Adaptive Motion Estimation for Elastography Using Ultrasound Sequences," IEEE Transactions on Medical Imaging, vol. 24, No. 6, Jun. 1, 2005, pp. 755-766.

Wagner et al., "Statistics of Speckle in Ultrasound B-Scans," IEEE Transactions on Sonics and Ultrasonics, vol. 30, No. 3, May 1983, pp. 156-163.

Wang et al., "Contrast Medium Assisted Fluid Flow Measurements," IEEE Transactions on Ultrasonics, Ferroelectric, and Frequency Control, vol. 42, No. 2, Mar. 1995, pp. 309-315.

Webster et al., "Measurement of Flow and Volume of Blood," Medical Instrumentation Application and Design, Wiley, 4th Edition, 2009, pp. 341-342.

Wilson et al., "Measurement of Two-Dimensional Blood Velocity Vectors by the Ultrasonic Speckle Projection Technique," Ultrasonic Imaging, vol. 15, 1993, pp. 286-303.

Xu, "Two-Dimensional Blood Flow Velocity Estimation Using Ultrasound Speckle Pattern Dependence on Scan Direction and Velocity," Aug. 1, 2012, 169 pages.

(56) References Cited

OTHER PUBLICATIONS

Shaw, C.G. et al., "Pulsed-injection method for blood flow velocity measurement in intraarterial digital subtraction angiography," Radio Radiological Society of North America, Inc., US, vol. 160, No. 2, Aug. 1, 1986, Abstract.

Holdsworth, D.W. et al., Quantitative antiographic blood-flow measurement using pulsed intra-arterial injection, the International Journal of Medical Physics Research and Practice, Oct. 1, 1999, retrieved on May 14, 2018 from https://aapm.onlinelibrary.wiley.com/doi/pdf/10.1118/1.598733, Abstract.

Olin, T. et al., "Spillover flowmeter: a preliminary report," From the Roentgendiagnostic Department University Hospital, Lund, Sweden, and The Department of Radiology Stanford University School of Medicine, Palo Alto, California, U.S.A. (1964). pp. 217-222, 5 pages.

Molloi, S. et al., "Estimation of coronary artery hyperemic blood flow based on arterial lumen volume using angiographic images," In. J. Cardio Imag. (2012), 28:1-11, 11 pages.

\* cited by examiner

ANGIOGRAM INJECTIONS USING ELECTROCARDIOGRAPHIC SYNCHRONIZATION

TECHNICAL FIELD

The disclosure relates to fluid injection systems.

BACKGROUND

Many medical imaging procedures, such as angiography, involve injecting a contrast fluid into a patient. Angiography is a procedure used in the diagnosis and treatment of cardiovascular conditions, including abnormalities or restrictions in blood vessels. During angiography, a radiographic image of the heart or vascular structure is obtained by injecting contrast fluid through a catheter into the vasculature (e.g., the coronary artery) of the patient. The injected contrast fluid can pass to vascular structures in fluid communication with the blood vessel in which the injection is made. X-rays are passed through the region of the body in which the contrast fluid was injected. The X-rays are absorbed by the contrast fluid, causing a radiographic outline or image of the vasculature containing the contrast fluid. Contrast injection can be used in conjunction with other medical procedures as well, such as optical coherence tomography (OCT) imaging, intravascular ultrasound (IVUS) imaging, computed tomography (CT) imaging, magnetic resonance imaging (MRI), and interventional device procedures/placements.

SUMMARY

In general, the disclosure describes techniques for synchronizing angiogram injections with an electrocardiogram in order to optimize the usage of the injection fluid. For instance, the injection system may read data indicative of an electrocardiogram to determine when a diastole begins. When the diastole begins, the injection system begins injecting fluid into the patient according to a diastolic injection phase (e.g., at a first rate corresponding to the diastolic injection phase and for the duration of the entire diastole). From that point onwards in the angiogram session, the injection system determines whether the difference between a dispensed volume limit (e.g., a maximum amount of fluid that can be injected into a patient in one injection) and a current volume of injection fluid that has already been dispensed from the fluid reservoir is large enough to complete both of a systolic injection phase and a diastolic injection phase while adhering to the dispensed volume limit after the completion of the previous diastolic injection phase. If the injection system determines that there is enough of a difference below the dispensed volume limit to complete both the systolic injection phase and the diastolic injection phase, then the injection system proceeds to perform the systolic injection phase and the diastolic injection phase upon completing the prior diastolic injection phase. Conversely, if the injection system determines that too much injection fluid has already been dispensed such that the injection system cannot complete both the next systolic injection phase and the next diastolic injection phase while remaining under the dispensed volume limit (e.g., the difference is only enough fluid to complete the systolic injection phase but not the diastolic injection phase, or there is not enough fluid to complete either phase), then the injection system refrains from performing either the systolic injection phase or the diastolic injection phase.

There are multiple benefits to the techniques described herein. For instance, the low pressure during the diastolic phases make it easier for injection fluid to reach the intended destination within the patient. As such, it is a more efficient use of the injection fluid to inject the injection fluid at a higher rate during the diastoles and a lower rate during the systoles. For this same reason, it is the most efficient use of the injection fluid to begin the injections during a beginning of a diastole to get the most benefit of the low-pressure diastole. Additionally, by verifying that a subsequent diastolic injection phase can be completed within the dispensed volume limit before performing the prior systolic injection phase, the injection system will not waste fluid by performing the systolic injection phase when the benefits of the diastolic injection phase cannot be completed. In these ways, the waste produced by injecting fluid into a patient when the higher-value injection cannot be completed is eliminated, instead saving that amount for future injections. As such, the techniques described herein maximize the amount of injection fluid that can be used during diastoles while eliminating the waste during other phases where the injection fluid is not as useful or during phases where the injection system cannot complete the entire injection. Techniques described herein involve injecting fluid during whole diastoles and intervening systoles but at no other times during the cardiac cycle.

In one example, the disclosure is directed to an injection system that includes a fluid reservoir configured to store an injection fluid. The injection system also includes one or more sensors configured to measure a volume of the injection fluid dispensed from the fluid reservoir. The injection system further includes one or more processors configured to receive, from the one or more sensors, a first group of one or more signals indicating a current volume of injection fluid dispensed from the fluid reservoir at a first time. The one or more processors are also configured to determine, based on the first group of one or more signals, that a first difference between a dispensed volume limit and the current volume of the injection fluid dispensed from the fluid reservoir at the first time is less than a necessary volume of fluid required to complete both a systolic injection phase and a diastolic injection phase. The one or more processors are further configured to, responsive to determining that the first difference is less than the necessary volume of fluid required to complete both the systolic injection phase and the diastolic injection phase, control the injection system to refrain from performing each of the systolic injection phase and the diastolic injection phase.

In another example, the disclosure is directed to a method that includes receiving, by one or more processors of an injection system and from one or more sensors, a first group of one or more signals indicating a current volume of injection fluid dispensed from a fluid reservoir at a first time. The method also includes determining, by the one or more processors and based on the first group of one or more signals, that a first difference between a dispensed volume limit and the current volume of the injection fluid dispensed from the fluid reservoir at the first time is less than a necessary volume of fluid required to complete both a systolic injection phase and a diastolic injection phase. The method further includes, responsive to determining that the first difference is less than the necessary volume of fluid required to complete both the systolic injection phase and the diastolic injection phase, refraining from performing each of the systolic injection phase and the diastolic injection phase.

In another example, the disclosure is directed to a non-transitory computer-readable storage medium containing instructions. The instructions, when executed, cause one or more processors of an injection system to receive, from one or more sensors, a first group of one or more signals indicating a current volume of injection fluid dispensed from a fluid reservoir at a first time. The instructions further cause the one or more processors to determine, based on the first group of one or more signals, that a difference between a dispensed volume limit and the current volume of the injection fluid dispensed from the fluid reservoir at the first time is less than a necessary volume of fluid required to complete both a systolic injection phase and a diastolic injection phase. The instructions also cause the one or more processors to, responsive to determining that the difference less than the necessary volume of fluid required to complete both the systolic injection phase and the diastolic injection phase, control the injection system to refrain from performing each of the systolic injection phase and the diastolic injection phase.

In another example, the disclosure is directed to a non-transitory computer-readable storage medium containing instructions that, when executed, cause one or more processors of an injection system to receive two or more injection characteristic inputs, wherein the two or more injection characteristic inputs comprise at least a number of images to be taken and an image quality input. The instructions further cause the one or more processors to determine, based on the two or more injection characteristic inputs, an injection schedule that includes a first flow rate for injection fluid during the diastolic injection phases and a second flow rate for injection fluid during systolic injection phases, wherein the injection schedule comprises an initial diastolic injection phase and one or more systolic/diastolic injection phase pairs, wherein each of the one or more systolic/diastolic injection phase pairs comprises a complete systolic injection phase and a complete diastolic injection phase, wherein the injection schedule ends with a complete diastolic injection phase portion of one of the one or more systolic/diastolic injection phase pairs, and wherein the first flow rate during each diastolic injection phase is based at least in part on the image quality input. The instructions also cause the one or more processors to control the injection system to inject injection fluid from a fluid reservoir of the injection system into a body of a patient according to the injection schedule.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
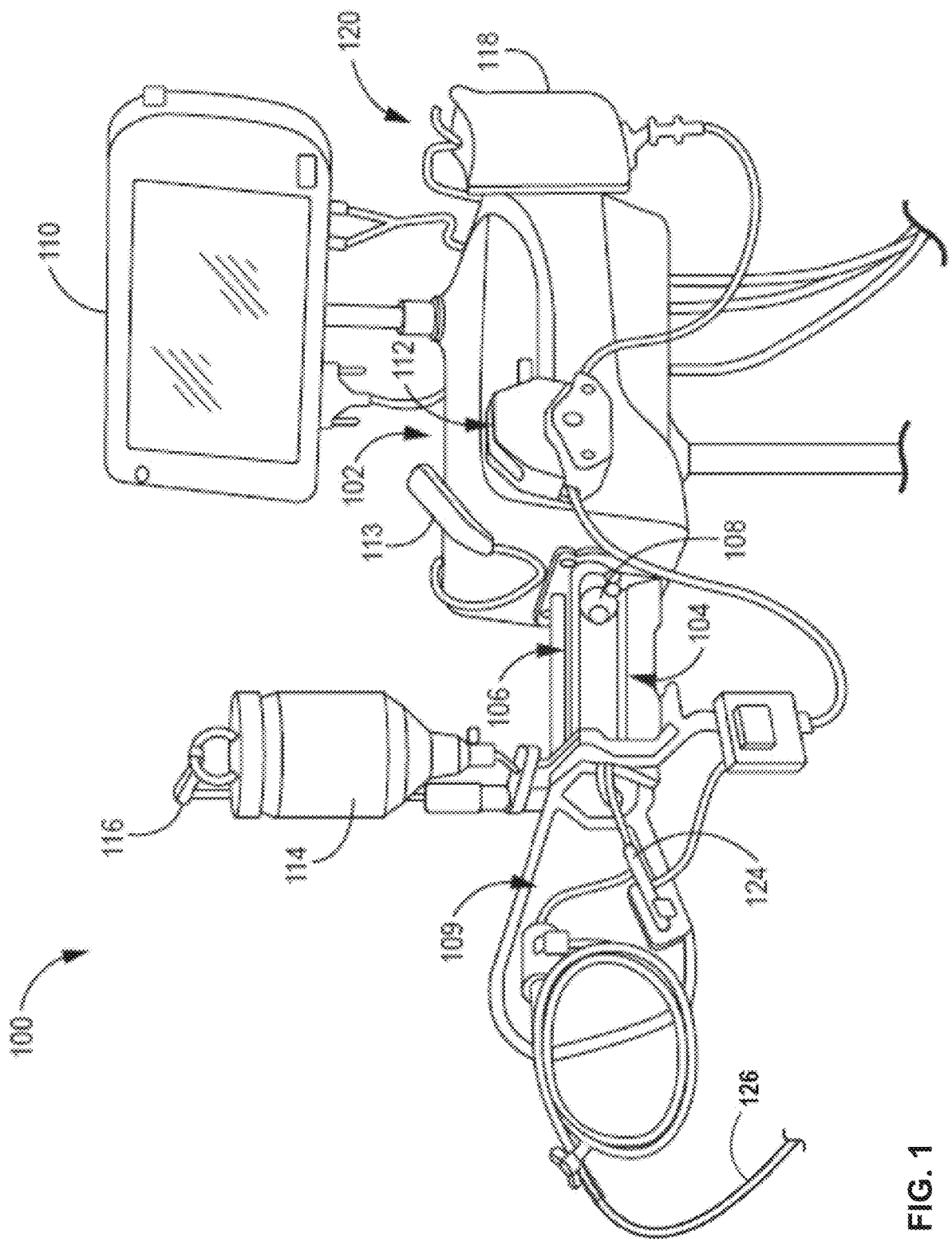
FIG. 1 illustrates a perspective view of an example of a powered fluid injector, in accordance with one or more aspects of the techniques described in this disclosure.

FIG. 1 is a perspective view of an example of a powered fluid injector 100, which may sometimes be referred to herein as the injection system 100. In operation, the powered fluid injector 100 can inject a quantity of fluid into a patient, for instance into a vessel of a patient via a catheter. The fluid injected by the powered fluid injector 100 can be, for example, a contrast fluid, a non-contrast fluid (e.g., saline), or a combination thereof. By injecting a quantity of fluid into a patient, the powered fluid injector 100 can facilitate a variety of medical diagnostic and/or interventional procedures, including the collection of image data representing an anatomical region of interest. These procedures can include, as examples, optical coherence tomography (OCT) imaging, intravascular ultrasound (IVUS) imaging, computed tomography (CT) imaging, magnetic resonance imaging (MRI), angiographic procedures, and interventional device procedures/placements.

The illustrated powered fluid injector 100 includes a drive assembly housing 102 (also referred to herein as an "injector housing") and a sleeve 104. The sleeve 104 can be secured to the drive assembly housing 102. For example, the drive assembly housing 102 can include an opening, and the sleeve 104 can be secured to the drive assembly housing 102 at or near such opening. The sleeve 104 may extend out from the drive assembly housing 102 and may be configured to receive and hold a reservoir 106 (also referred to herein as a "fluid reservoir"). The reservoir 106 can have an internal reservoir volume containing a fluid and can include a plunger 108 within the internal reservoir volume. Plunger 108 may be made of various components, including a wiper configured to be proximally and distally movable within the interior of fluid reservoir 106 and a ram extending from drive assembly housing 102 into sleeve 104 and being configured to engage the wiper when fluid reservoir 106 is received and secured in sleeve 104 and to drive the wiper proximally and distally in accordance with instructions received from controller 110 coupled to drive assembly housing 102. At least a portion of a drive assembly can be housed within the drive assembly housing 102.

The drive assembly can be configured to pressurize fluid within the internal reservoir volume. For instance, the drive assembly may couple to the plunger 108, such as at the opening in the drive assembly housing 102, and drive the plunger 108 within the internal reservoir volume. As the plunger 108 is progressively driven within the fluid reservoir 106, fluid within the internal reservoir volume can be output from the fluid reservoir 106 along tubing 109 leading to a catheter 126 that is inserted into a patient's blood vessel to inject the fluid into the vasculature. In certain applications of the powered fluid injector 100, output fluid, such as contrast media, can be pressurized anywhere from 1000-1500 psi (e.g., 1200 psi).

The illustrated example of the powered fluid injector 100 includes several features that can be useful in pressurizing and delivering fluid during operation. The powered fluid injector 100 can include a controller 110. The controller 110 can include a user interface for various operational aspects. For example, the controller 110 can be utilized by a user to set up various parameters and/or protocols to be used for a given fluid injection procedure. In one example, the user can interact with the controller 110 to input fluid injection parameters such as flow rate, injection volume (e.g., maximum), injection pressure limit (e.g., maximum), fluid injection duration, rise time, and/or other injection parameters. In one example, the controller 110 includes a touch-screen panel display, enabling a user to view and modify injection parameters. The controller 110 can also be used to initialize the powered fluid injector 100 (e.g., to prepare it for a patient fluid injection), or to activate certain features or sequences of operation. The controller 110 may also provide status information, including information related to past or currently ongoing injection procedures as well as any appropriate alerts. The controller 110 can include an imaging engine having one or more processors for controlling operation of the powered fluid injector 100. Such processors can also control other components, such as the drive assembly, a peristaltic pump 112, when present, and/or any sensors and detectors included at the powered fluid injector 100.

In addition to the controller 110, the illustrated powered fluid injector 100 includes a hand-control device 113 for user input. The hand-control device 113 can be coupled to the powered fluid injector 100 and the controller 110 either wirelessly or via a lined connection. As shown, the hand-control device 113 connects to drive assembly housing 102. In other examples, the hand-control device 113 can be connected directly to the controller 110. The hand-control device 113 can generate and send various signals related to an injection procedure to the controller 110 or other connected component. A user can actuate one or more interface components at the hand-control device 113 to control an injection procedure. For example, the user can use hand-control device 113 as a variable-rate control device to alter the fluid flow rate output from the powered fluid injector 100 and/or as a mechanism for starting or stopping a fluid injection. Hand-control device 113 may include an exterior body of the controller that is sized to be held in a single hand of a user. In other instances, hand-control device 113 may be sized differently, such as to be held in two hands of the user or to sit on a surface during operation.

The powered fluid injector 100 can also include one or more components useful for supplying fluid to be used in an injection procedure. A container 114 can include a supply of fluid, such as contrast media, and be secured to a holder 116 at the powered fluid injector 100. Fluid from the container 114 can be supplied to the fluid reservoir 106 for use during an injection procedure. For example, fluid from the container 114 can be drawn into the fluid reservoir 106 when the plunger 108 is being retracted and thereby refill the internal reservoir volume. Similarly, when the powered fluid injector 100 includes the peristaltic pump 112, a second container 118 can include a supply of fluid, such as a flushing medium (e.g., saline), and be secured to a holder 120 at the powered fluid injector 100. When present, the peristaltic pump 112 can receive fluid from the second container 118 and deliver such fluid to the patient. Often times, the peristaltic pump 112 may be used to deliver non-contrast fluid, such as saline, at a lower pressure than that at which the drive assembly delivers contrast fluid from the fluid reservoir 106. A valving system 124 can be included to selectively place the fluid reservoir 106 or peristaltic pump 112 in communication with the patient.

As described elsewhere herein, the controller 110 of the powered fluid injector 100 may control various functions of the powered fluid injector 100, which may include dispensing contrast fluid out through tubing. In some examples, the controller 110 may be housed in a housing of a display device. In some examples, the controller may be housed in the injector housing.

The powered fluid injector 100 may be connected to a catheter 126, fluidly and electrically, that is inserted into a blood vessel (e.g., the coronary artery) of a patient. When so connected, the powered fluid injector 100 can inject contrast fluid (of various concentrations) or dispense non-contrast fluid into the patient's vasculature via the injector tubing and the catheter 126. In many examples, the catheter 126 may include an invasive blood pressure sensor. The blood pressure sensor may be in electrical communication with the controller 110 when the powered fluid injector 100 is connected to the catheter 126. The blood pressure sensor may provide a blood pressure signal to the controller 110 when the catheter 126 is in fluidic connection with the powered fluid injector 100 and may not provide a blood pressure signal when the catheter 126 is not in fluidic connection with the powered fluid injector 100.

In accordance with the techniques described herein, injection system 100 may be modified to perform one or more of the techniques described herein. For instance, injection system 100 may receive, from one or more sensors that are configured to read fluid levels within fluid reservoir 106, a first group of one or more signals indicating a current volume of injection fluid dispensed from fluid reservoir 106 at a first time. Injection system 100 may determine, based on the first group of one or more signals, whether a first difference between a dispensed volume limit and the current volume of the injection fluid dispensed from fluid reservoir 106 at the first time is less than a necessary volume of fluid required to complete both a systolic injection phase (e.g., a reduced-rate injection of the injection fluid into the patient throughout the duration of a systole for a patient) and a diastolic injection phase (e.g., a higher-rate injection of the injection fluid into the patient throughout the duration of a diastole for a patient). If injection system 100 determines that the first difference indicates that there is a large enough difference between the dispensed volume limit and the current volume of injection fluid dispensed from fluid reservoir 106 such that injection system 100 may complete both the next systolic injection phase and the next diastolic injection phase, injection system 100 may proceed to perform both the next systolic injection phase and the next diastolic injection phase. Conversely, responsive to determining that the first difference is less than the necessary volume of fluid required to complete both the systolic injection phase and the diastolic injection phase, injection system 100 refrains from performing each of the systolic injection phase and the diastolic injection phase. In other words, if there is not enough fluid such that injection system 100 may complete both of the next systolic injection phase and the next diastolic injection phase while still adhering to the dispensed volume limit, injection system 100 will perform neither of the next systolic injection phase and the next diastolic injection phase, instead ceasing the injection process at the completion of the previous diastolic injection phase.

Injection system 100 may also receive inputs that the injection system may use to define an injection schedule that similarly refrains from performing partial systolic or diastolic injection phases if those phases cannot be completed under the necessary criteria. For instance, injection system 100 may receive two or more injection characteristic inputs, such as a number of images to be taken and an image quality input. Injection system 100 may also determine, based on the two or more injection characteristic inputs, an injection schedule that includes a first flow rate for injection fluid during the diastolic injection phases and a second flow rate for injection fluid during the systolic injection phases. The injection schedule may also include an initial diastolic injection phase and one or more systolic/diastolic injection phase pairs, with each of the one or more systolic/diastolic injection phase pairs including a complete systolic injection phase and a complete diastolic injection phase. The injection schedule ends with a complete diastolic injection phase portion of one of the one or more systolic/diastolic injection phase pairs. The first flow rate during the diastolic injection phases is based at least in part on the image quality input. Injection system 100 may inject injection fluid from a fluid reservoir of the injection system into a body of a patient according to the injection schedule.

Implementing the techniques described herein into powered fluid injector 100 as described herein provides multiple benefits. For instance, the low pressure during the diastolic phases makes it easier for injection fluid to reach the intended destination within the patient when injected by powered fluid injector 100. As such, it is a more efficient use of the injection fluid to inject the injection fluid at a higher rate during the diastoles and a slower rate during the systoles. For this same reason, it is the most efficient use of the injection fluid to begin the injections during a beginning of a diastole to get the most benefit of the low-pressure diastole. Additionally, by verifying that a subsequent diastolic injection phase can be completed within the dispensed volume limit before performing the prior systolic injection phase, powered fluid injector 100 will not waste fluid by performing the systolic injection phase when the benefits of the diastolic injection phase cannot be completed while also increasing patient safety by ensuring that the dispensed volume limit is not exceeded. In these ways, the waste produced by injecting fluid into a patient when the higher-value injection cannot be completed is eliminated, instead saving that amount for future injections. As such, the techniques described herein maximize the amount of injection fluid that can be used during diastoles while eliminating the waste during other phases where the injection fluid is not as useful or during phases where powered fluid injector 100 cannot complete the entire injection.

Figure 2:
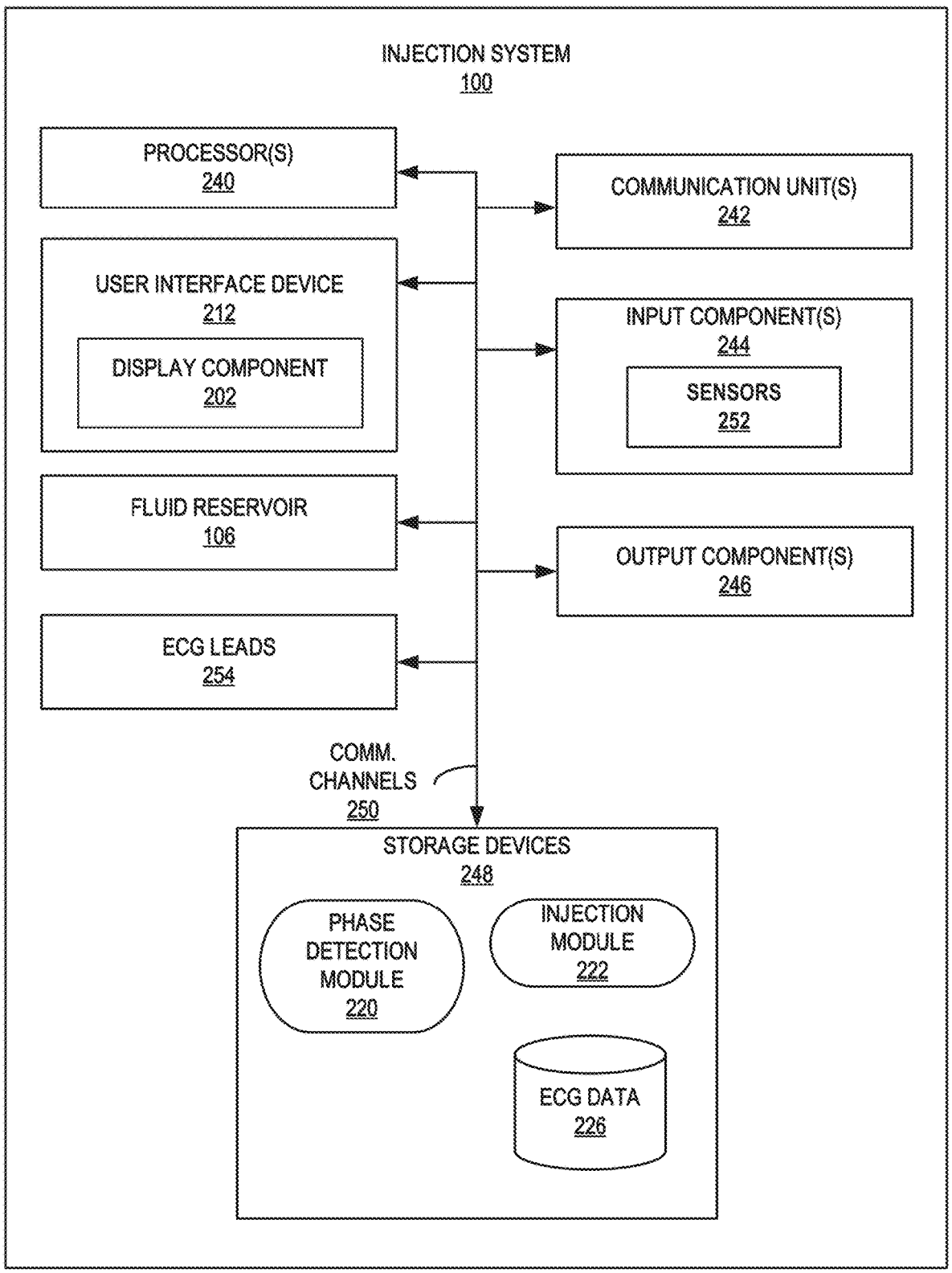
FIG. 2 is a block diagram illustrating a more detailed example of an injection system configured to perform the techniques described herein.

FIG. 2 is a block diagram illustrating an example computing device configured to synchronize an angiography injection schedule with an electrocardiogram, in accordance with one or more aspects of the techniques described in this disclosure. Injection system 100 of FIG. 2 is described below as an example of injection system 100 of FIG. 1. FIG. 2 illustrates only one particular example of injection system 100, and many other examples of injection system 100 may be used in other instances and may include a subset of the components included in example injection system 100 or may include additional components not shown in FIG. 2.

As shown in the example of FIG. 2, injection system 100 includes user interface device (UID) 212, one or more processors 240, one or more communication units 242, one or more input components 244, one or more output components 246, and one or more storage components 248. UID 212 includes display component 202. Storage components 248 of injection system 100 include phase detection module 220, injection module 222, and electrocardiogram data 226.

One or more processors 240 may implement functionality and/or execute instructions associated with injection system 100 to dynamically expand an interface element associated with an application displayed on UID 212 of injection system 100. That is, processors 240 may implement functionality and/or execute instructions associated with injection system 100 to synchronize angiogram injections with an electrocardiogram of the patient in a way that refrains from performing partial injections, in accordance with the techniques described herein.

Examples of processors 240 include application processors, display controllers, auxiliary processors, one or more sensor hubs, and any other hardware configure to function as a processor, a processing unit, or a processing device. Modules 220 and 222 may be operable by processors 240 to perform various actions, operations, or functions of injection system 100. For example, processors 240 of injection system 100 may retrieve and execute instructions stored by storage components 248 that cause processors 240 to perform the operations described with respect to modules 220 and 222. The instructions, when executed by processors 240, may cause injection system 100 to synchronize angiogram injections with an electrocardiogram of the patient in a way that refrains from performing partial injections, in accordance with the techniques described herein.

Phase detection module 220 may perform operations for managing electrocardiogram data 226, for example, for synchronizing the angiogram injection to follow various diastoles and systoles present in electrocardiogram data 226 for time frames defined by electrocardiogram data 226. For example, phase detection module 220 of injection system 100 may receive electrocardiogram data 226, analyze electrocardiogram data 226 to separate out various diastoles and systoles present in electrocardiogram data, and analyze the diastoles and systoles to determine one or more representative characteristics of diastoles and systoles for a particular patient.

Injection module 222 of injection system 100 may perform operations for controlling injections provided by injection system 100 and various characteristics of the injections. For instance, injection module 222 may control when injections begin, when injections end, and the various injection flow rates, in addition to making other determinations with regards to fluid injections, as described throughout this disclosure.

In some examples, phase detection module 220 and injection module 222 may execute locally (e.g., at processors 240) to provide functions associated with injection system 100. In some examples, phase detection module 220 and injection module 222 may act as an interface to a remote service accessible to injection system 100.

One or more storage components 248 within injection system 100 may store information for processing during operation of injection system 100 (e.g., injection system 100 may store data accessed by modules 220 and 222 during execution at injection system 100). In some examples, storage component 248 is a temporary memory, meaning that a primary purpose of storage component 248 is not long-term storage. Storage components 248 on injection system 100 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage components 248, in some examples, also include one or more computer-readable storage media. Storage components 248 in some examples include one or more non-transitory computer-readable storage mediums. Storage components 248 may be configured to store larger amounts of information than typically stored by volatile memory. Storage components 248 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 248 may store program instructions and/or information (e.g., data) associated with modules 220 and 222 and electrocardiogram data 226. Storage components 248 may include a memory configured to store data or other information associated with modules 220 and 222 and electrocardiogram data 226.

Electrocardiogram data 226 may be any data indicative of an electrocardiogram of a patient. In some instances, electrocardiogram data 226 may be numerical data indicative of the electrical impulses measured or recorded by a plurality of electrocardiogram leads, such as electrocardiogram leads 254. In other instances, electrocardiogram data 226 may be an image of the electrocardiogram that is analyzed through graphical analysis performed by phase detection module 220. In still other instances, rather than electrocardiogram leads 254 being a mechanical part of injection system 100, electrocardiogram leads 254 may be communicatively coupled to injection system 100 via a hemodynamic system that facilitates communication between the two.

Communication channels 250 may interconnect each of the components 212, 240, 242, 244, 246, 248, and 254 for inter-component communications (physically, communicatively, and/or operatively). In some examples, communication channels 250 may include a system bus, a network connection, an inter-process communication data structure, or any other method for communicating data.

One or more communication units 242 of injection system 100 may communicate with external devices via one or more wired and/or wireless networks by transmitting and/or receiving network signals on one or more networks. Examples of communication units 242 include a network interface card (e.g. such as an Ethernet card), an optical transceiver, a radio frequency transceiver, a GPS receiver, or any other type of device that can send and/or receive information. Other examples of communication units 242 may include short wave radios, cellular data radios, wireless network radios, as well as universal serial bus (USB) controllers.

One or more input components 244 of injection system 100 may receive input. Examples of input are tactile, audio, and video input. Input components 244 of injection system 100, in one example, includes a presence-sensitive input device (e.g., a touch sensitive screen, a PSD), mouse, keyboard, voice responsive system, camera, microphone or any other type of device for detecting input from a human or machine. In some examples, input components 244 may include one or more sensor components 252 one or more location sensors (GPS components, Wi-Fi components, cellular components), one or more temperature sensors, one or more movement sensors (e.g., accelerometers, gyros), one or more pressure sensors (e.g., barometer), one or more ambient light sensors, and one or more other sensors (e.g., infrared proximity sensor, hygrometer sensor, and the like). Other sensors, to name a few other non-limiting examples, may include a heart rate sensor, magnetometer, glucose sensor, olfactory sensor, compass sensor, step counter sensor.

Sensors 252 may also include fluid sensors either in communication with or incorporated into fluid reservoir 106. In this manner, sensors 252 may measure a current volume of injection fluid within fluid reservoir 106 and transmit one or more signals to injection module 222 with an indication of the determined current volume.

One or more output components 246 of injection system 100 may generate output in a selected modality. Examples of modalities may include a tactile notification, audible notification, visual notification, machine generated voice notification, or other modalities. Output components 246 of injection system 100, in one example, includes a presence-sensitive display, sound card, video graphics adapter card, speaker, cathode ray tube (CRT) monitor, liquid crystal display (LCD), or any other type of device for generating output to a human or machine in a selected modality.

UID 212 of injection system 100 may include display component 202. Display component 202 may be a screen at which information (e.g., a visual indication) is displayed by UID 212. Display component 202 may also detect an object at and/or near display component 202, such as like a presence-sensitive display.

While illustrated as an internal component of injection system 100, UID 212 may also represent an external component that shares a data path with injection system 100 for transmitting and/or receiving input and output. For instance, in one example, UID 212 represents a built-in component of injection system 100 located within and physically connected to the external packaging of injection system 100 (e.g., a screen on a mobile phone). In another example, UID 212 represents an external component of injection system 100 located outside and physically separated from the packaging or housing of injection system 100 (e.g., a monitor, a projector, etc. that shares a wired and/or wireless data path with injection system 100).

UID 212 of injection system 100 may detect two-dimensional and/or three-dimensional gestures as input from a user of injection system 100. For instance, a sensor of UID 212 may detect a user's movement (e.g., moving a hand, an arm, a pen, a stylus, tactile object, etc.) within a threshold distance of the sensor of UID 212. UID 212 may determine a two or three-dimensional vector representation of the movement and correlate the vector representation to a gesture input (e.g., a hand-wave, a pinch, a clap, a pen stroke, etc.) that has multiple dimensions. In other words, UID 212 can detect a multi-dimension gesture without requiring the user to gesture at or near a screen or surface at which UID 212 outputs information for display. Instead, UID 212 can detect a multi-dimensional gesture performed at or near a sensor which may or may not be located near the screen or surface at which UID 212 outputs information for display.

While not necessarily included in every example of injection system 100, in some examples, injection system 100 may also include electrocardiogram leads 254. In such examples, electrocardiogram leads 254 may be electrodes configured to be attached to a patient in order to develop an electrocardiogram for the patient, such as producing electrocardiogram data 226. Accordingly, electrocardiogram leads 254 may provide electrocardiogram data 226 to injection system 100, enabling injection system 100 to perform the techniques described herein in a self-contained environment and in real time. In other examples, communication unit 242 may receive electrocardiogram data 226 from a separate server, system, or database outside of injection system 100, such as a hemodynamic system coupled to injection system 100 and electrocardiogram leads 254.

In accordance with the techniques described herein, in some instances, injection module 222 may control injection system 100 to perform an initial diastolic injection phase.

Injection module 222 may control injection system 100 in this way in response to receiving an indication of user input at input components 244 to begin a fluid injection process. Phase detection module 220 may then detect, based on electrocardiogram data 226 of the patient, a beginning of a diastole. Responsive to phase detection module 220 detecting the beginning of the diastole, injection module 222 controls injection system 100 to begin injecting the injection fluid from the fluid reservoir according to the initial diastolic injection phase.

After the initial diastolic injection phase, and after every subsequent diastolic injection phase, injection module 222 may receive, from sensors 252, a first group of one or more signals indicating a current volume of injection fluid dispensed from fluid reservoir 106 at a first time. This current volume dispensed from fluid reservoir 106 may mean an amount of fluid that injection system 100 has already injected into the current patient in a current injection. Injection module 222 may determine, based on the first group of one or more signals, whether a first difference between a dispensed volume limit and the current volume of the injection fluid dispensed from fluid reservoir 106 at the first time is less than a necessary volume of fluid required to complete both a systolic injection phase and a diastolic injection phase. The dispensed volume limit may be either pre-defined or user defined as a maximum amount of injection fluid that may be injected from injection system 100 into a patient during any one injection. Exceeding this dispensed volume limit may have detrimental effects on the patient, so it is recommended that the user of the injection system not exceed this dispensed volume limit when imaging parts of the patient.

In some instances, injection module 222 may determine, based on the first group of one or more signals, that a first difference between a dispensed volume limit and the current volume of the injection fluid dispensed from fluid reservoir 106 at the first time is not less than the necessary volume of fluid required to complete both the systolic injection phase and the diastolic injection phase. In such instances, responsive to determining that the first difference is greater than or equal to than the necessary volume of fluid required to complete both the systolic injection phase and the diastolic injection phase, injection module 222 controls injection system 100 to perform both the systolic injection phase and the diastolic injection phase.

In performing the systolic injection phase and the diastolic injection phase, phase detection module 220 may detect, from electrocardiogram data 226 of the patient, a beginning of a systole. Responsive to phase detection module 220 detecting the beginning of the systole, injection module 222 controls the injection system to begin injecting the injection fluid from the fluid reservoir into the patient at a first rate, as defined by the systolic injection phase. Phase detection module 220 may then detect, from electrocardiogram data 226 of the patient, an ending of the systole and a beginning of a diastole. Responsive to phase detection module 220 detecting the beginning of the diastole, injection module 222 controls injection system 100 to stop injecting the injection fluid according at the first rate and begin injecting the injection fluid from the fluid reservoir at a second rate different than the first rate, the second rate corresponding to and defined by the diastolic injection phase.

The first rate of the injection during the systolic injection phase may be less than the second rate of an injection during the diastolic injection phase. The blood pressure during a systole is greater than the blood pressure during a diastole. As such, to take advantage of the relative ease of pushing the injection fluid into the correct location at a time of lower blood pressure as compared to the higher blood pressure systoles, injection module 222 may control injection system 100 to inject fluid at a greater rate during diastolic injection phases than during systolic injection phases. For instance, the rate of fluid injection during a systole may be some percentage of the fluid injection rate during a diastole. In some instances, the fluid flow rate during systole may be zero. In some instances, the fluid flow rate during systole may vary between the beginning of systole and the end of systole (e.g., ramping down from the higher diastole rate at the beginning of systole to a minimum value and then ramping back up toward the higher diastole rate at the end of systole). Similarly, the fluid flow rate during diastole may vary between the beginning of diastole and the end of diastole.

Injection module 222 may calculate the diastolic injection rate for the diastolic injection phase based on numerous factors. These factors could include at least the dispensed volume limit, a user defined flow rate, a number of diastolic cycles to be imaged, and an image quality level. For instance, if a dispensed volume limit is 6 mL of fluid, and the user wishes for at least three diastolic cycles to be imaged, injection module 222 may adjust the diastolic injection rate such that enough fluid of the 6 mL volume limit remains for at least three diastolic injection phases to be completed.

Phase detection module 220 may determine the beginning and end of systoles and diastoles through analyzing electrocardiogram data 226. For instance, a systole occurs when the heart muscles contract, thereby pushing blood out of the heart. A systole is shown in electrocardiograms, such as the examples of FIGS. 3A-3E and FIG. 4 by short, sharp increases in the blood pressure, as shown in the peaks of the electrocardiogram. Meanwhile, a diastole occurs when the heart muscle relaxes, thereby allowing blood to fill the various chambers of the heart. A diastole is shown in electrocardiograms as a longer period of relatively unchanging, or slighter, slopes. Phase detection module 220 may analyze electrocardiogram data 226 to determine when a patient is experiencing a systole and when a patient is experiencing a diastole.

In instances where electrocardiogram data may not be available in real-time, phase detection module 220 may determine characteristics of previous diastoles and systoles for a patient and utilize that information in the phase detection aspects of this disclosure. For instance, phase detection module 220 may determine, based on either the numerical or graphical data present in electrocardiogram data 226, an average systole length and an average diastole length for the patient. In such instances, phase detection module 220 may use the average time lengths to determine when to switch between systolic injection phases and diastolic injection phases. For example, after detecting the beginning of the systole, phase detection module 220 may determine that an amount of time equal to the average systole length has passed since detecting the systole.

Injection module 222 may also determine the first rate and the second rate based on electrocardiogram data 226. For instance, injection module 222 may determine that a certain amount of injection fluid should be injected into the patient during a diastole and/or a systole for the patient. Using the corresponding diastole or systole average length computed by phase detection module 220, injection module 222 may determine the correct rate for the diastolic injection phase and/or the systolic injection phase by dividing the determined amount of injection fluid that should be injected into the patient by the average length of the corresponding phase.

Conversely, injection module 222 may determine, based on the first group of one or more signals, that the first difference is less than the necessary volume of fluid required to complete both the systolic injection phase and the diastolic injection phase. Responsive to determining that the first difference is less than the necessary volume of fluid required to complete both the systolic injection phase and the diastolic injection phase, injection module 222 may control injection system 100 to refrain from performing each of the systolic injection phase and the diastolic injection phase.

In one or more additional examples, either in addition to or in place of the techniques described above with respect to FIG. 2, injection module 222 may receive inputs and may use those inputs to define an injection schedule that similarly refrains from performing partial systolic or diastolic injection phases if those phases cannot be completed under the necessary criteria. For instance, injection module 222 may receive two or more injection characteristic inputs, such as a number of images to be taken and an image quality. Additional injection characteristic inputs could include a maximum injection flow rate, a dispensed volume limit, injection power ratios, average diastole lengths, and average systole lengths. In some instances, the image quality input may specify the flow rate of injection fluid during the diastolic injection phases, as the flow rate of injection fluid affects how light or dark a corresponding image will be. In some instances, the image quality input may be a value on a scale (e.g., 10 being highest quality and 1 being lowest quality) or other subjective image quality input. In such instances, the injection module 222 may determine the flow rate of injection fluid during the diastolic injection phases based on the image quality input and one or more anatomical characteristics of the patient.

Injection module 222 may also determine, based on the two or more injection characteristic inputs, an injection schedule that includes a first flow rate for injection fluid during diastolic injection phases and a second flow rate for injection fluid during systolic injection phases. The second flow rate may be a percentage less than the first flow rate. The injection schedule may also include an initial diastolic injection phase and one or more systolic/diastolic injection phase pairs, with each of the one or more systolic/diastolic injection phase pairs including a complete systolic injection phase and a complete diastolic injection phase. In some instances, the number of images taken may correlate to the number of diastolic injection phases (e.g., one image may be taken during each diastolic injection phase). The injection schedule ends with a complete diastolic injection phase portion of one of the one or more systolic/diastolic injection phase pairs. The first flow rate during the diastolic injection phases is based at least in part on the image quality input.

In some instances, injection module 222 may further adjust the injection schedule based on a maximum injection limit for the injection fluid such that a total volume of injection fluid dispensed according to the injection schedule is less than or equal to the maximum injection limit. In doing so, injection module 222 may, if the total volume of injection fluid dispensed according to the injection schedule is greater than the maximum injection limit, remove one or more systolic/diastolic injection phase pairs until the total volume of injection fluid used during the initial diastolic injection phase and the remaining systolic/diastolic injection phase pairs is less than or equal to the maximum injection limit. The maximum injection limit may be an organizationally or individually set limit to the amount of injection fluid that can be injected into a patient during an imaging session while still being safe for the patient.

Injection module 222 may inject injection fluid from a fluid reservoir of the injection system into a body of a patient according to the injection schedule. In some instances, injection module 222 may, prior to beginning the injection according to the initial diastolic injection phase, control injection system 200 to begin a leading injection to increase a fluid pressure within injection system 200.

In some instances, in controlling injection system 200 to inject the injection fluid, during each systolic/diastolic injection phase pair, phase detection module 220 may detect, from an electrocardiogram of the patient, a beginning of a systole. Responsive to phase detection module 220 detecting the beginning of the systole, injection module 222 may control the injection system to begin injecting the injection fluid from the fluid reservoir into the patient at the second rate. Phase detection module 220 may then detect, from the electrocardiogram of the patient, an ending of the systole and a beginning of a diastole. Responsive to phase detection module 220 detecting the beginning of the diastole, injection module 222 may control injection system 200 to stop injecting the injection fluid at the first rate and begin injecting the injection fluid from the fluid reservoir at the first rate. In some instances, in detecting the shifts between systoles and diastoles, phase detection module 220 may receive data descriptive of the electrocardiogram and determine, based on the data descriptive of the electrocardiogram, an average systole length for the patient. After detecting the beginning of the systole, phase detection module 220 may determine that an amount of time equal to the average systole length has passed since detecting the systole.

Figure 3A:
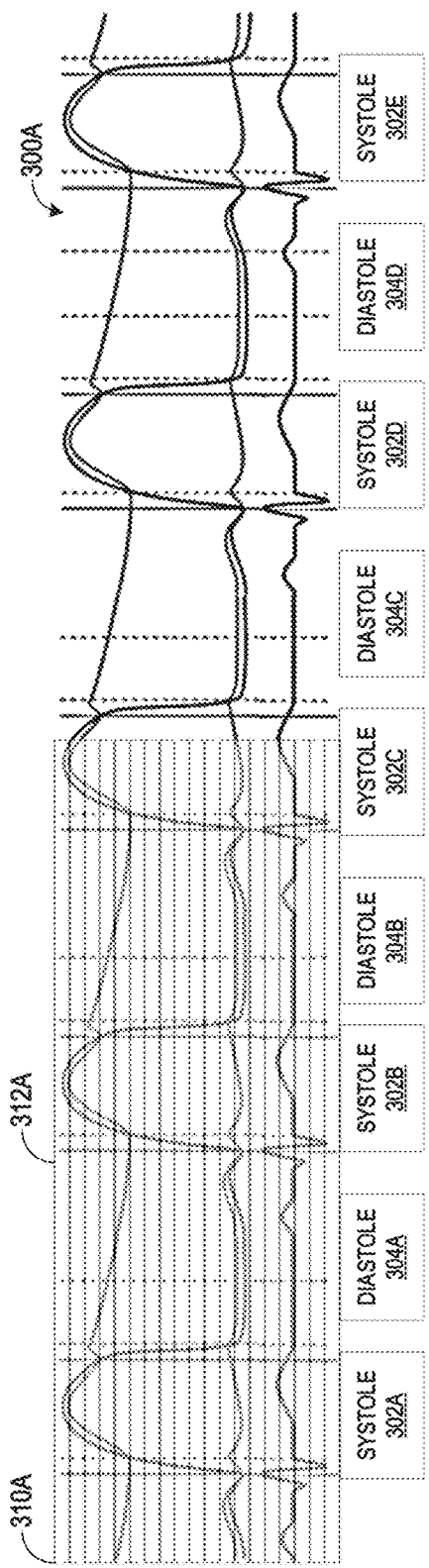
FIGS. 3A-3E are example electrocardiograms illustrated with overlays of injection schedules in accordance with prior angiography techniques.

FIGS. 3A-3E are example electrocardiograms 300A-300E illustrated with overlays of injection schedules in accordance with prior angiography techniques. The example of FIG. 3A depicts a traditional injection method that delivers a prescribed volume of fluid at a continuous rate. The total volume of fluid will be delivered during injection phase 312A without considerations of systoles 302A-302E or diastoles 304A-304D. Injection phase 312A will begin at time 310A, upon receipt of an indication of user input to begin (e.g., via the touch-screen or the hand control button), and will continue until the amount of injection fluid injected into the patient reaches the dispensed volume limit.

Figure 3B:
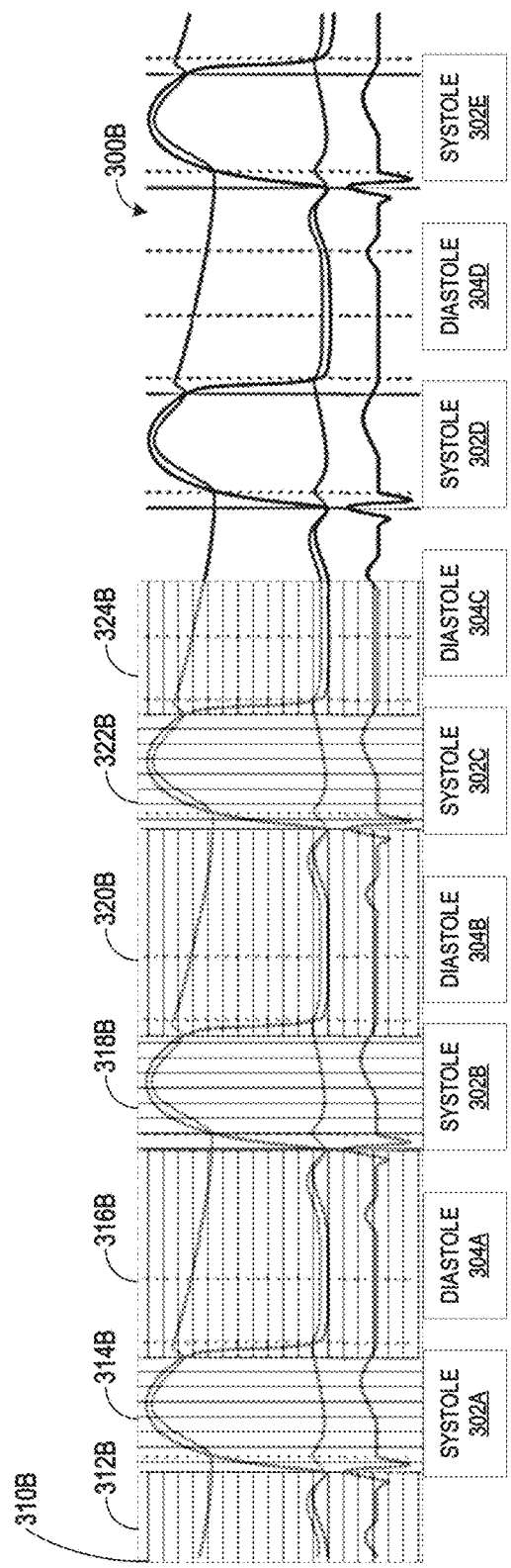

FIG. 3B shows electrocardiogram 300B with a basic electrocardiogram synchronization injection. In the example of FIG. 3B, the injection begins upon receipt of an indication of user input to begin at time 310B, and begins with diastolic injection phase 312B. This process will then reduce power during systoles 302A-302C to save contrast injected during systolic injection phases 314B, 318B, and 322B. The power will return to full power during diastolic injection phases 316B, 320B, and 324B. This allows a user to inject the same amount of contrast over a longer time duration, but will still deliver the full requested volume (e.g., up to the dispensed volume limit). These techniques would reduce the total requested volume from their standard injection parameters. However, systolic injection phases 314B, 318B, and 322B are of lesser imaging value because of the increased blood pressure as discussed herein. Similarly, injections for partial diastoles can be of lesser imaging value, meaning that diastolic injection phase 312B and diastolic injection phase 324B are not as valuable as diastolic injection phase 316B or diastolic injection phase 320B in angiographic procedures.

Figure 3C:
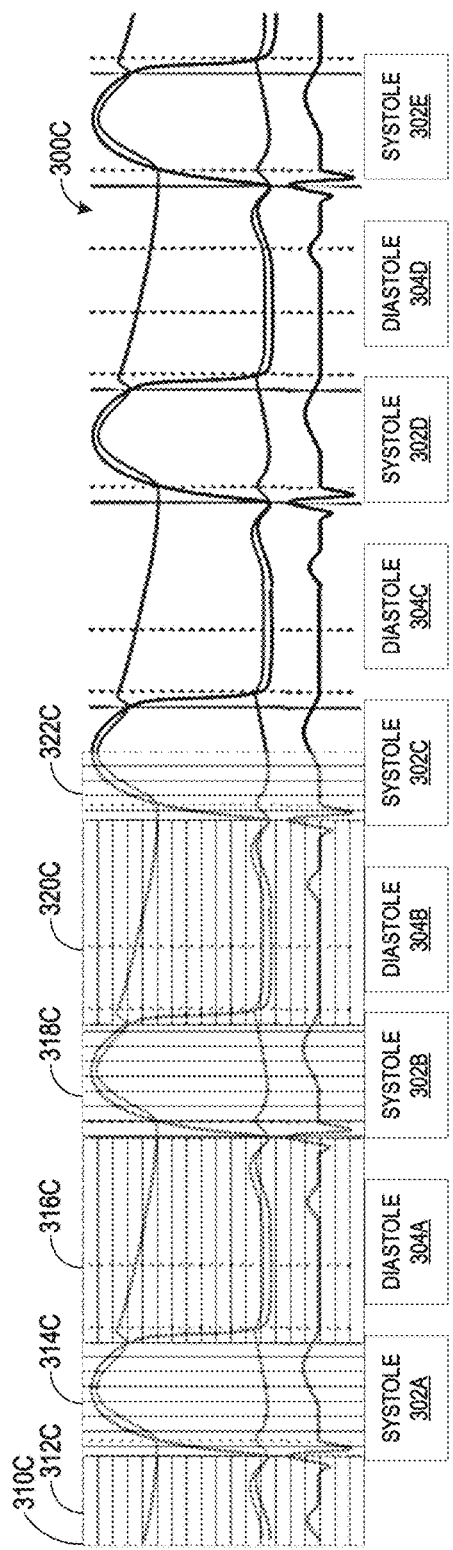

FIG. 3C shows electrocardiogram 300C with a clip synced injection. In the example of FIG. 3C, the injection begins upon receipt of an indication of user input to begin at time 310C, and begins with diastolic injection phase 312C. This process will then reduce power during systoles 302A-302C to save contrast injected during systolic injection phases 314C, 318C, and 322C. The power will return to full power during diastolic injection phases 316C and 320C. However, this mode will only deliver contrast for the time duration of an equivalent un-synced injection. For example, if a 3 mL/s injection with a dispensed volume limit of 6 mL takes 2 seconds to fully deliver, this mode will deliver contrast for 2 seconds with reduced power during systole. This reduces the total amount of contrast delivered, but still has wasted contrast on the leading (312C, 314C) and trailing (322C) ends.

Figure 3D:
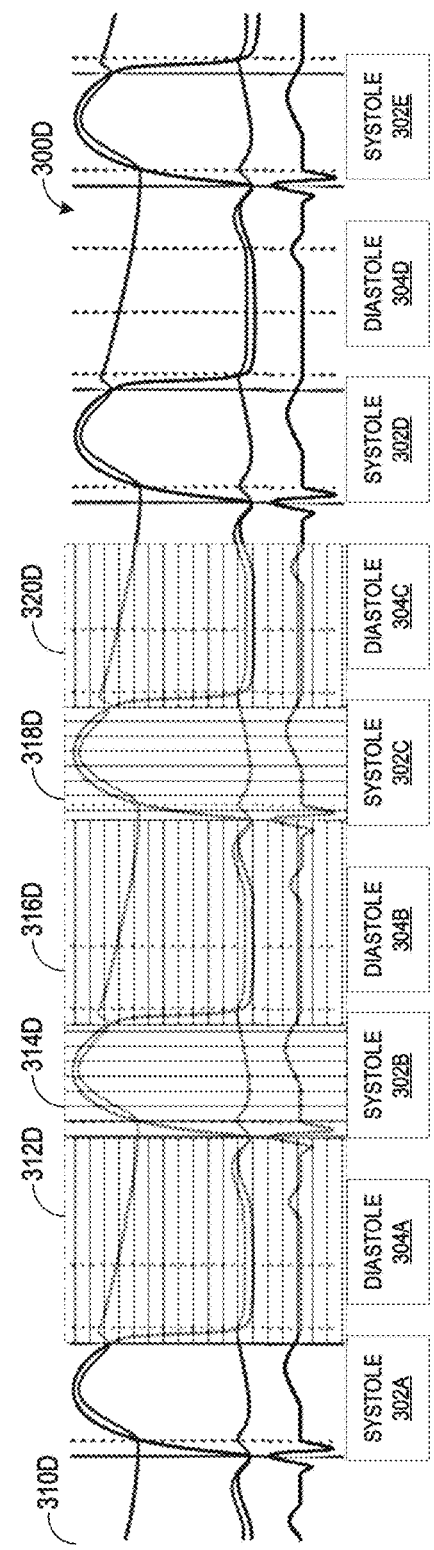

FIG. 3D shows electrocardiogram 300D with a delayed and clip synced injection. In the example of FIG. 3D, the injection does not begin upon receipt of an indication of user input to begin at time 310D, instead delaying the injection until the first detected diastole 304A and beginning diastolic injection phase 312D. This process will still reduce power during systoles 302B-302C to save contrast injected during systolic injection phases 314D and 318D. The power will return to full power during diastolic injection phases 316D and 320D. Delayed and clip-synced mode is the same as a clip-synced injection in FIG. 3C except the start point is delayed until the next diastolic onset. This prevents any contrast waste on the leading edge of an injection. However, this technique still injects for the un-synced time equivalent (e.g., 2 seconds) which still allows for contrast waste on the trailing end of the injection with systolic injection phase 318D and partial diastolic injection phase 320D.

Figure 3E:
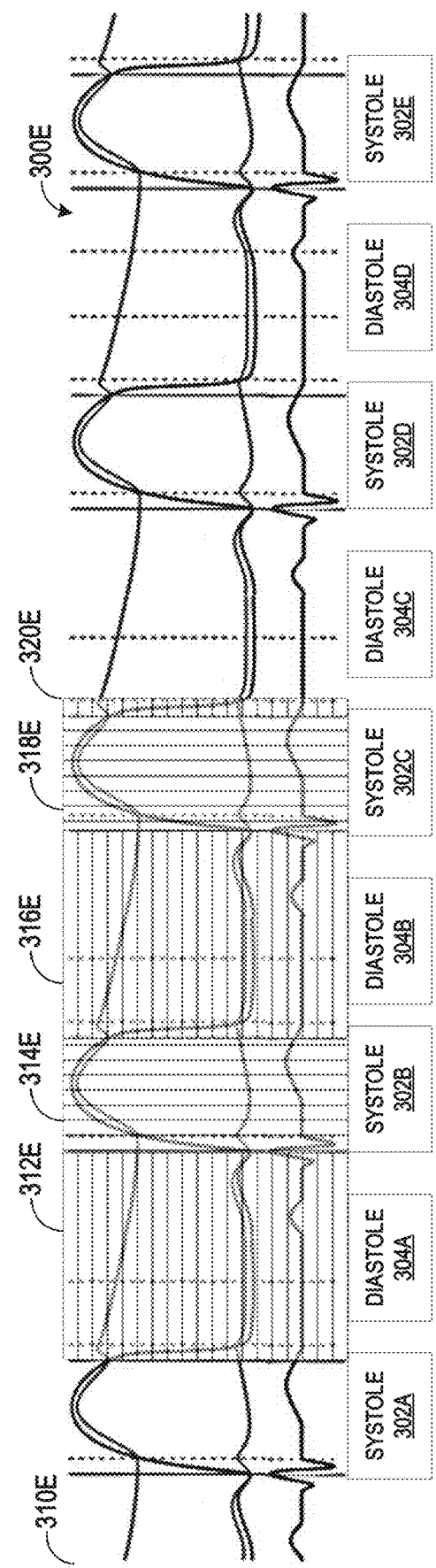

FIG. 3E shows electrocardiogram 300E with a delayed and clip synced injection with reduced volume. In the example of FIG. 3E, the injection does not begin upon receipt of an indication of user input to begin at time 310E, instead delaying the injection until the first detected diastole 304A and beginning diastolic injection phase 312E. This process will still reduce power during systoles 302B-302C to save contrast injected during systolic injection phases 314E and 318E. The power will return to full power during diastolic injection phases 316E and 320E. However, this is a manual process controlled by a user of the fluid injection system. For instance, the injection system will determine if the next systole 302 or diastole 304 will be completed in the limited time frame available under the delayed and clip synced method. If there is not enough time to complete the next systole 302 or diastole 304, the injection may cease. However, this may still waste contrast fluid in a trailing edge if the final injection is a systole (e.g., systolic injection phase 318E), wasting injection fluid in the final phase (e.g., diastolic injection phase 320E).

Figure 4:
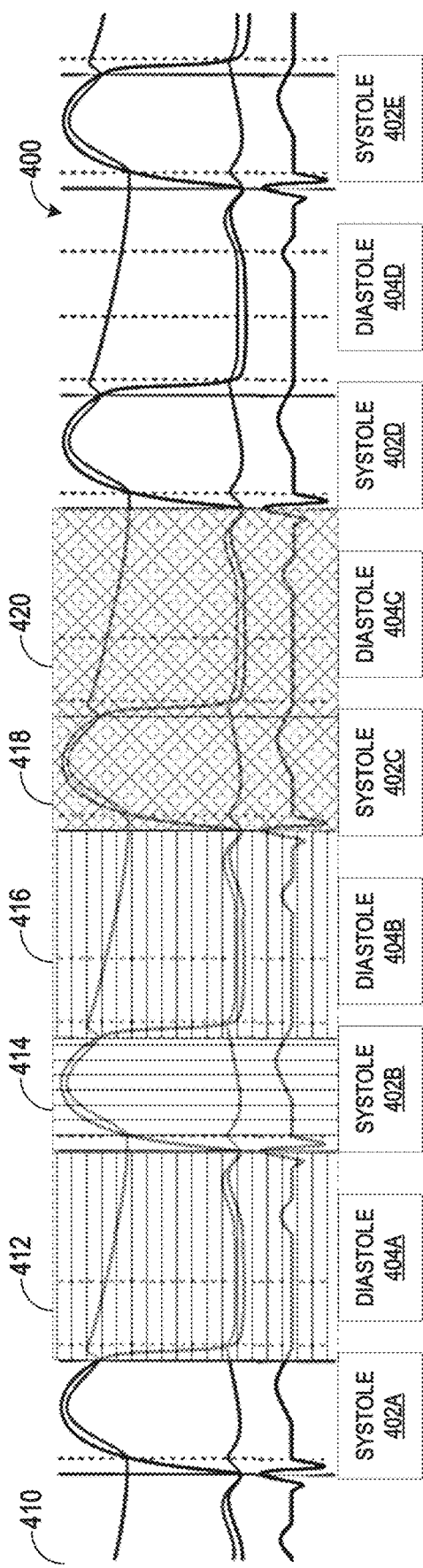
FIG. 4 is an example electrocardiogram illustrated with overlays of an angiography injection schedule in accordance with one or more of the techniques described herein.

FIG. 4 is an example electrocardiogram illustrated with overlays of an angiography injection schedule in accordance with one or more of the techniques described herein. FIG. 4 shows electrocardiogram 400 with an optimized synced injection in accordance with the techniques described herein. In the example of FIG. 4, the injection does not begin upon receipt of an indication of user input to begin at time 410, instead delaying the injection until the injection system detects the beginning of diastole 404A. Once the injection system detects the beginning of diastole 404A, the injection begins with the initial diastolic injection phase 412.

After diastolic injection phase 412, the injection system determines if the difference between the dispensed volume limit and the current volume of injection fluid dispensed from the fluid reservoir in the current injection is sufficient to complete both systolic injection phase 414 during systole 402B (at the reduced power) and diastolic injection phase 416 during diastole 404B (at the normal power). In this example, the injection system determines that the difference is large enough that the injection system may complete both systolic injection phase 414 and diastolic injection phase 416 while adhering to the dispensed volume limit. As such, the injection system performs both of systolic injection phase 414 and diastolic injection phase 416.

After diastolic injection phase 416, the injection system determines if the difference between the dispensed volume limit and the current volume of injection fluid dispensed from the fluid reservoir in the current injection is sufficient to complete both systolic injection phase 418 during systole 402C (at the reduced power) and diastolic injection phase 420 during diastole 404C (at the normal power). While there may be enough of a difference under the dispensed volume limit to complete systolic injection phase 418, in the example of FIG. 4, the injection system determines that there is an insufficient amount of available injection fluid under the dispensed volume limit to complete diastolic injection phase 420. As such, the injection system refrains from performing either of systolic injection phase 418 and diastolic injection phase 420.

In general, the optimized synced injection is essentially a delayed start and clipped injection, but the clipping is done differently. Instead of clipping the injection based on a time equivalence, it clips based on whether or not the amount of volume already injected into the patient is sufficiently less than the dispensed volume limit such that the injection system may complete another diastolic injection phase while adhering to the dispensed volume limit. For example, in the example of FIG. 4, there may only be 1.2 mL of a difference between what has already been injected into the patient and what the dispensed volume limit is at the onset of the final diastolic injection phase 420. This is less than the required 1.5 mL needed in this example to complete the final diastolic injection phase 420, so the injection will be halted. Since the final diastolic injection phase 420 will not take place, the final systolic injection phase 418 will also be eliminated, as an injection during a systole is not valuable if a full diastolic injection phase is not subsequently completed. This type of sequence eliminates leading and trailing waste while still capturing the same two full diastolic phases that would be captured with a traditional injection.

In some examples, the injection system may be operated in fixed mode or variable mode. In fixed mode, the injection system may operate in accordance with a schedule programmed in the controller. In variable mode, a user may control injection through the hand controller. When in variable mode, one or more processors may set a maximum flow rate as the dispensed volume limit approaches. In this way, the user can be prevented from increasing the flow rate to the point of inadvertently reaching the dispensed volume limit during a systolic injection phase or during a partial diastolic phase. The maximum flow rate in variable mode during the latter part of an injection sequence can help ensure that the injection sequence ends at the end of a diastolic injection phase, thereby minimizing waste.

Fluid may be injected according to a schedule that involves injecting only during full diastolic phases (i.e., not fractions of diastolic phases) and any intervening systolic phases. In some examples, the user may input the flow rate and the desired number of images to be taken (e.g., one per diastolic cycle). As an alternative, the user could input a desired image quality level instead of a flow rate and allow the system to select the appropriate flow rate based on one or more anatomical characteristics of the patient. For instance, using any of these, or other, characteristics, the injection system may determine an injection schedule that includes initial diastolic injection phase 412, and a systolic/diastolic injection phase pair that includes systolic injection phase 414 and diastolic injection phase 416. In other words, injection phases 412, 414, and 416 may be determined as a schedule preemptively, and the injection system may follow that schedule.

Figure 5:
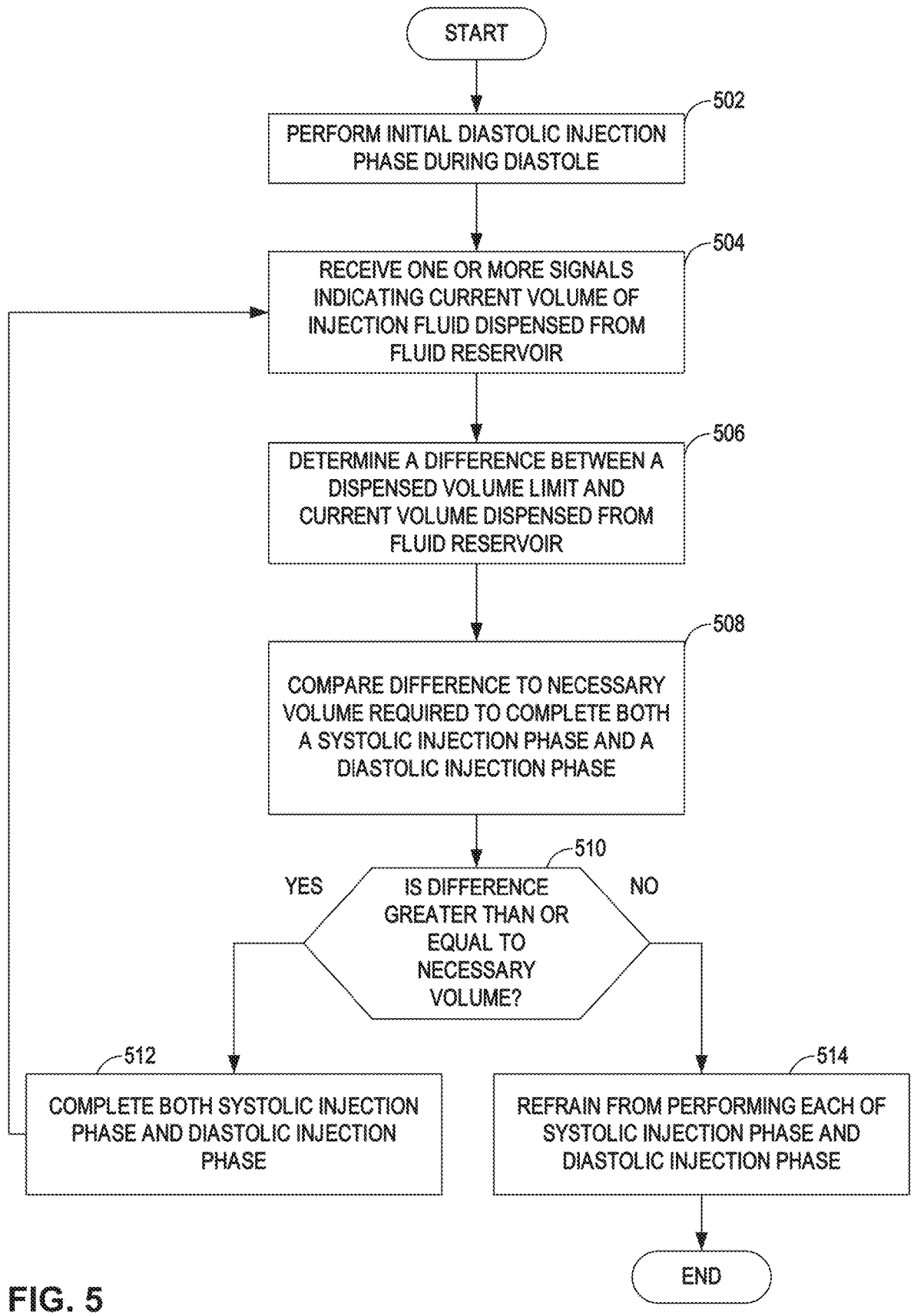
FIG. 5 is a flow chart illustrating an example angiography injection process for an injection system configured to synchronize the injection with an electrocardiogram, in accordance with one or more aspects of the techniques described in this disclosure.

FIG. 5 is a flow chart illustrating an example angiography injection process for an injection system configured to synchronize the injection with an electrocardiogram, in accordance with one or more aspects of the techniques described in this disclosure. The techniques of FIG. 5 may be performed by one or more processors of a device, such as injection system 100 of FIG. 1 and/or injection system 100 illustrated in FIG. 2. For purposes of illustration only, the techniques of FIG. 5 are described within the context of injection system 100 of FIG. 2, although devices having configurations different than that of injection system 100 may perform the techniques of FIG. 5.

Injection module 222 controls injection system 100 to perform an initial diastolic injection phase during a diastole of the patient (502). Injection module 222 then measures a volume of injection fluid dispensed from fluid reservoir 106 by receiving, from sensors 252, a first group of one or more signals indicating a current volume of injection fluid dispensed from fluid reservoir 106 at a first time (504). Injection module 222 then determines a difference between a dispensed volume limit and the current volume of injection fluid dispensed from fluid reservoir 106 (506) and compares the difference to a necessary volume of injection fluid required to complete both a systolic injection phase and another diastolic injection phase (508).

Injection module 222 determines, based on the first group of one or more signals, whether the difference is greater than or equal to the necessary volume of fluid required to complete both the systolic injection phase and the diastolic injection phase (510). Responsive to determining that the difference between the dispensed volume limit and the current volume of injection fluid dispensed from fluid reservoir 106 is greater than or equal to the necessary volume of fluid required to complete both the systolic injection phase and the diastolic injection phase ("YES" branch of 510), injection module 222 controls injection system 100 to complete both the systolic injection phase and the diastolic injection phase (512). Injection module 222 then receives subsequent signals with updated information on the volume of fluid dispensed from fluid reservoir 106 (504), and the process continues.

Conversely, responsive to determining that the difference between the dispensed volume limit and the current volume of injection fluid dispensed from fluid reservoir 106 is less than the necessary volume of fluid required to complete both the systolic injection phase and the diastolic injection phase ("NO" branch of 510), injection module 222 controls the injection system to refrain from performing each of the systolic injection phase and the diastolic injection phase (514).

Figure 6:
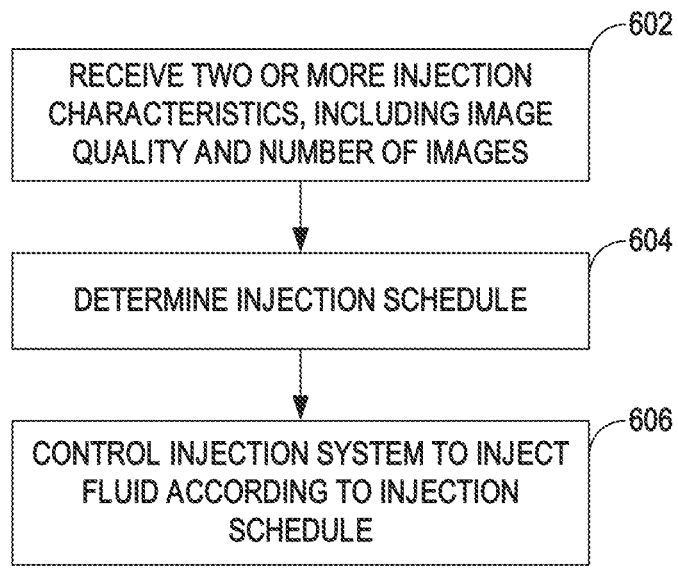
FIG. 6 is a flow chart illustrating an example angiography injection process for an injection system configured to synchronize an injection schedule with an electrocardiogram, in accordance with one or more aspects of the techniques described in this disclosure.

FIG. 6 is a flow chart illustrating an example angiography injection process for an injection system configured to synchronize the injection with an electrocardiogram, in accordance with one or more aspects of the techniques described in this disclosure. The techniques of FIG. 6 may be performed by one or more processors of a device, such as injection system 100 of FIG. 1 and/or injection system 100 illustrated in FIG. 2. For purposes of illustration only, the techniques of FIG. 6 are described within the context of injection system 100 of FIG. 2, although devices having configurations different than that of injection system 100 may perform the techniques of FIG. 6.

For instance, injection module 222 may receive two or more injection characteristic inputs, including an image quality input and a number of images to be taken (e.g., one image per diastolic injection phase) (602). In some examples, the image quality input specifies the injection flow rate. In some examples, the image quality input may be a value on a scale (e.g., 10 being highest quality and 1 being lowest quality) or other subjective image quality input. In such instances, the injection module 222 may determine the flow rate of injection fluid during the diastolic injection phases based on the image quality input and one or more anatomical characteristics of the patient. These injection characteristic inputs may also include a maximum injection flow rate, a dispensed volume limit, injection power ratios, average diastole lengths, and average systole lengths. Injection module 222 may determine, based on the two or more injection characteristic inputs, an injection schedule that includes a number of diastolic injection phases equal to the number of images to be taken, a first flow rate for injection fluid during the diastolic injection phases, and a second flow rate for injection fluid during each systolic injection phase (604). The second flow rate may be a percentage less than the first flow rate. The injection schedule may also include an initial diastolic injection phase and one or more systolic/diastolic injection phase pairs, with each of the one or more systolic/diastolic injection phase pairs including a complete systolic injection phase and a complete diastolic injection phase. The injection schedule ends with a complete diastolic injection phase portion of one of the one or more systolic/diastolic injection phase pairs. The first flow rate during each diastolic injection phase is based at least in part on the image quality. Injection module 222 may then control injection system 100 to inject the injection fluid into a body of a patient according to the injection schedule (606), ending the injection at the completion of the final systolic/diastolic injection pair.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

Various examples of the disclosure have been described. Any combination of the described systems, operations, or functions is contemplated. These and other examples are within the scope of the following claims.

What is claimed is:

1. An injection system comprising:
    a fluid reservoir configured to store an injection fluid;
    one or more sensors configured to measure a volume of the injection fluid dispensed from the fluid reservoir; and
    one or more processors configured to:
        receive, from the one or more sensors, a first group of one or more signals indicating a current volume of the injection fluid dispensed from the fluid reservoir at a first time;
        determine, based on the first group of one or more signals, that a first difference between a dispensed volume limit and the current volume of the injection fluid dispensed from the fluid reservoir at the first time is less than a necessary volume of fluid required to complete both a systolic injection phase and a diastolic injection phase; and
        responsive to determining that the first difference is less than the necessary volume of fluid required to complete both the systolic injection phase and the diastolic injection phase, control the injection system to refrain from performing each of the systolic injection phase and the diastolic injection phase even if the first difference is enough to complete the systolic injection phase.

2. The injection system of claim 1, wherein the one or more processors are further configured to:
    receive, from the one or more sensors, a second group of one or more signals indicating a current volume of the injection fluid dispensed from the fluid reservoir at a second time before the first time;
    determine, based on the second group of one or more signals, that a second difference between the dispensed volume limit and the current volume of the injection fluid dispensed from the fluid reservoir at the second time is not less than the necessary volume of fluid required to complete both the systolic injection phase and the diastolic injection phase; and
    responsive to determining that the second difference is not less than the necessary volume of fluid required to complete both the systolic injection phase and the diastolic injection phase, control the injection system to perform both the systolic injection phase and the diastolic injection phase.

3. The injection system of claim 2, wherein the one or more processors being configured to perform the systolic injection phase and the diastolic injection phase comprises the one or more processors being configured to:
    detect, from an electrocardiogram of a patient, a beginning of a systole;
    responsive to detecting the beginning of the systole, control the injection system to begin injecting the injection fluid from the fluid reservoir into the patient at a first rate;
    detect, from the electrocardiogram of the patient, an ending of the systole and a beginning of a diastole; and
    responsive to detecting the beginning of the diastole, control the injection system to stop injecting the injection fluid at the first rate and begin injecting the injection fluid from the fluid reservoir at a second rate different than the first rate.

4. The injection system of claim 3, wherein the first rate is less than the second rate.

5. The injection system of claim 3, wherein the injection system is communicatively connected to a hemodynamic system, which received the electrocardiogram from a plurality of electrocardiogram leads configured to record the electrocardiogram.

6. The injection system of claim 3, wherein the one or more processors are further configured to:
    receive data descriptive of the electrocardiogram; and
    determine, based on the data descriptive of the electrocardiogram, an average systole length for the patient, wherein the one or more processors being configured to detect the ending of the systole and the beginning of the diastole comprises the one or more processors being configured to, after detecting the beginning of the systole, determine that an amount of time equal to the average systole length has passed since detecting the systole.

7. The injection system of claim 6, wherein the one or more processors are further configured to determine the first rate and the second rate based on the data descriptive of the electrocardiogram.

8. The injection system of claim 1, wherein the one or more processors are further configured to, prior to the first time, control the injection system to perform an initial diastolic injection phase.

9. The injection system of claim 8, wherein the one or more processors being configured to control the injection system to perform the initial diastolic injection phase comprises the one or more processors being configured to:
receive an indication of user input to begin a fluid injection process;
detect, based on an electrocardiogram of a patient, a beginning of a diastole; and
responsive to detecting the beginning of the diastole, control the injection system to begin injecting the injection fluid from the fluid reservoir according to the initial diastolic injection phase.

10. The injection system of claim 1, wherein the dispensed volume limit comprises a maximum amount of injection fluid that can be injected into a patient.

11. A method comprising:
receiving, by one or more processors of an injection system and from one or more sensors, a first group of one or more signals indicating a current volume of injection fluid dispensed from a fluid reservoir at a first time;
determining, by the one or more processors and based on the first group of one or more signals, that a first difference between a dispensed volume limit and the current volume of the injection fluid dispensed from the fluid reservoir at the first time is less than a necessary volume of fluid required to complete both a systolic injection phase and a diastolic injection phase; and
responsive to determining that the first difference is less than the necessary volume of fluid required to complete both the systolic injection phase and the diastolic injection phase, refraining from performing each of the systolic injection phase and the diastolic injection phase even if the first difference is enough to complete the systolic injection phase.

12. The method of claim 11, further comprising:
receiving, by the one or more processors and from the one or more sensors, a second group of one or more signals indicating the current volume of the injection fluid dispensed from the fluid reservoir at a second time before the first time;
determining, by the one or more processors, based on the second group of one or more signals, that a second difference between the dispensed volume limit and the current volume of the injection fluid dispensed from the fluid reservoir at the second time is not less than the necessary volume of fluid required to complete both the systolic injection phase and the diastolic injection phase; and
responsive to determining that the second difference is not less than the necessary volume of fluid required to complete both the systolic injection phase and the diastolic injection phase, controlling, by the one or more processors, the injection system to perform both the systolic injection phase and the diastolic injection phase.

13. The method of claim 12, wherein performing the systolic injection phase and the diastolic injection phase comprises:
detecting, by the one or more processors, from an electrocardiogram of a patient, a beginning of a systole;
responsive to detecting the beginning of the systole, controlling, by the one or more processors, the injection system to begin injecting the injection fluid from the fluid reservoir into the patient at a first rate;
detecting, by the one or more processors from the electrocardiogram of the patient, an ending of the systole and a beginning of a diastole; and
responsive to detecting the beginning of the diastole, controlling, by the one or more processors, the injection system to stop injecting the injection fluid according at the first rate and begin injecting the injection fluid from the fluid reservoir at a second rate different than the first rate.

14. The method of claim 13, wherein the first rate is less than the second rate.

15. The method of claim 13, further comprising:
receiving, by the one or more processors, data descriptive of the electrocardiogram; and
determining, by the one or more processors, based on the data descriptive of the electrocardiogram, an average systole length for the patient,
wherein detecting the ending of the systole and the beginning of the diastole comprises, after detecting the beginning of the systole, determining, by the one or more processors, that an amount of time equal to the average systole length has passed since detecting the systole.

16. The method of claim 15, further comprising determining, by the one or more processors, the first rate and the second rate based on the data descriptive of the electrocardiogram.

17. The method of claim 11, further comprising, prior to the first time, controlling, by the one or more processors, the injection system to perform an initial diastolic injection phase.

18. The method of claim 17, wherein controlling the injection system to perform the initial diastolic injection phase comprises:
receiving, by the one or more processors, an indication of user input to begin a fluid injection process;
detecting, by the one or more processors, based on an electrocardiogram of a patient, a beginning of a diastole; and
responsive to detecting the beginning of the diastole, controlling, by the one or more processors, the injection system to begin injecting the injection fluid from the fluid reservoir according to the initial diastolic injection phase.

19. The method of claim 11, wherein the dispensed volume limit comprises a maximum amount of injection fluid that can be injected into a patient.

20. A non-transitory computer-readable storage medium containing instructions that, when executed, cause one or more processors to:
calculate a difference between a dispensed volume limit and a volume of injection fluid previously dispensed from a fluid reservoir of an injection system;

prior to performing a systolic injection phase, verify that the calculated difference is not less than a volume of injection fluid required to perform both the systolic injection phase and a subsequent diastolic injection phase; and control the injection system to perform both the systolic injection phase and the subsequent diastolic injection phase only in response to verifying that the calculated difference is not less than the volume of injection fluid required to perform both the systolic injection phase and the subsequent diastolic injection phase;

a wherein in response to failing to verify that the calculated difference is not less than the volume of injection fluid required to perform both the systolic injection phase and the subsequent diastolic injection phase, neither the systolic injection phase nor the subsequent diastolic injection phase are performed even if the calculated difference is sufficient to perform the systolic injection phase.

21. The non-transitory computer-readable storage medium of claim 20, wherein the volume of injection fluid previously dispensed is measured by one or more sensors of the injection system.

22. The non-transitory computer-readable storage medium of claim 20, wherein the volume of injection fluid previously dispensed was previously dispensed during a prior diastolic injection phase.

23. The non-transitory computer-readable storage medium of claim 20, wherein the dispensed volume limit comprises a maximum amount of injection fluid that can be injected into a patient.

24. The non-transitory computer-readable storage medium of claim 20, wherein the dispensed volume limit is pre-defined.

25. The non-transitory computer-readable storage medium of claim 20, wherein the dispensed volume limit is user defined.

26. The non-transitory computer-readable storage medium of claim 20, wherein an injection rate applied during the systolic injection phase is different from an injection rate applied during the subsequent diastolic injection phase.

27. The non-transitory computer-readable storage medium of claim 20, wherein the instructions, when executed, further cause the one or more processors to determine a start of the systolic injection phase and a start of the subsequent diastolic injection phase from electrocardiogram data.

* * * * *